United States Patent

Borzatta et al.

[11] Patent Number: 5,726,226
[45] Date of Patent: Mar. 10, 1998

[54] PEPERIDINE COMPOUNDS CONTAINING SILANE GROUPS AS STABILIZERS FOR ORGANIC MATERIALS

[75] Inventors: Valerio Borzatta, Bologna; Primo Carrozza, Verona, both of Italy

[73] Assignee: Ciba Specialty Chemcials Corporation, Tarrytown, N.Y.

[21] Appl. No.: 836,949

[22] PCT Filed: Nov. 18, 1995

[86] PCT No.: PCT/EP95/04546

§ 371 Date: May 22, 1997

§ 102(e) Date: May 22, 1997

[87] PCT Pub. No.: WO96/17002

PCT Pub. Date: Jun. 6, 1996

[30] Foreign Application Priority Data

Nov. 30, 1994 [IT] Italy .................. MI94A2428

[51] Int. Cl.$^6$ .................. C07F 7/18; C08G 77/26
[52] U.S. Cl. .................. 524/102; 524/99; 525/102; 546/14
[58] Field of Search .................. 524/99, 102; 525/102; 546/14

[56] References Cited

FOREIGN PATENT DOCUMENTS

| | | | |
|---|---|---|---|
| 0388321 | 9/1990 | European Pat. Off. | 524/102 |
| 0491659 | 6/1992 | European Pat. Off. | 524/102 |
| 4407947 | 9/1994 | Germany | 524/102 |

*Primary Examiner*—Zinna Northington Davis
*Attorney, Agent, or Firm*—Luther A. R. Hall

[57] ABSTRACT

Compounds of formula (I)

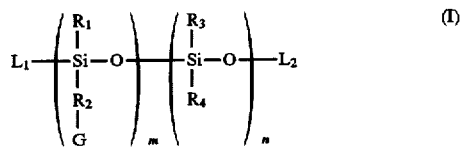

in which m+n is a number from 1 to 100 and n varies from zero to 90% of the sum of m+n; $R_1$ and $R_3$, which may be identical or different, are for example $C_1$–$C_{18}$alkyl or phenyl; $R_2$ is $C_2$–$C_{12}$alkylene; G is for example a group of formula (IId)

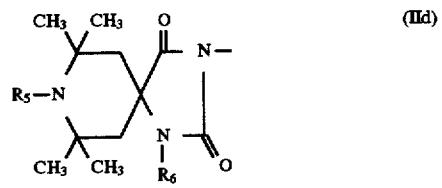

in which $R_5$ and $R_6$ are for example hydrogen; $R_4$ is for example $C_1$–$C_{18}$alkyl; $L_1$ has for example any one of the meanings given to $R_1$ or is a group $(R_{28})_3SiO$— where $R_{28}$ is $C_1$–$C_{18}$alkyl; and $L_2$ is for example hydrogen, Na, K, $C_1$–$C_8$alkyl or a group $(R_{28})_3Si$— with $R_{28}$ as defined above.

The compounds of formula (I) are useful as light, heat and oxidation stabilizers for organic materials.

11 Claims, No Drawings

PEPERIDINE COMPOUNDS CONTAINING SILANE GROUPS AS STABILIZERS FOR ORGANIC MATERIALS

This application is a 371 of PCT/EP95/04546 filed Nov. 18, 1995.

The present invention relates to novel piperidine compounds containing silane groups, their use as light, heat and oxidation stabilizers for organic materials, especially synthetic polymers, and to organic materials thus stabilized.

The use of derivatives of 2,2,6,6-tetramethylpiperidine that contain silane groups, such as those noted in patents U.S. Pat. No. 4,177,186, U.S. Pat. No. 4,859,759, U.S. Pat. No. 4,895,885, U.S. Pat. No. 4,946,880, U.S. Pat. No. 4,948,888, U.S. Pat. No. 5,134,233, U.S. Pat. No. 5,219,905, U.S. Pat. No. 5,321,066, EP-A-162 524, EP-A-182 415, EP-A-244 026, EP-A-343 717, EP-A-388 321, EP-A-480 466, DD-A-234 682 and DD-A-234 683, as stabilizers for synthetic polymers is known.

The present invention relates to novel compounds of formula (I)

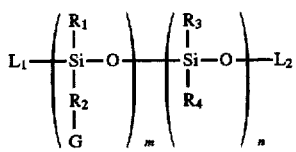

in which m+n is a number from 1 to 100 and n varies from zero to 90% of the sum of m+n;

$R_1$ and $R_3$, which may be identical or different, are $C_1$–$C_{18}$alkyl, phenyl, $C_1$–$C_8$alkoxy, OH, ONa or OK;

$R_2$ is $C_2$–$C_{12}$alkylene;

G is one of the groups of formula (IIa)–(IId)

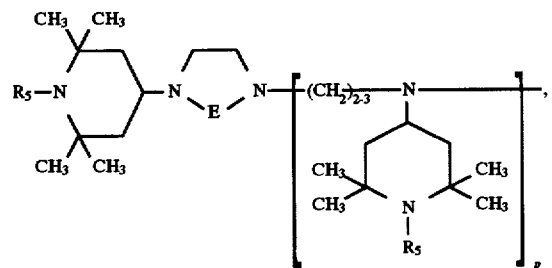

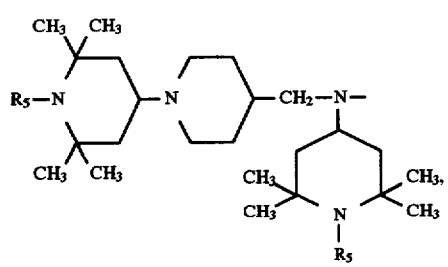

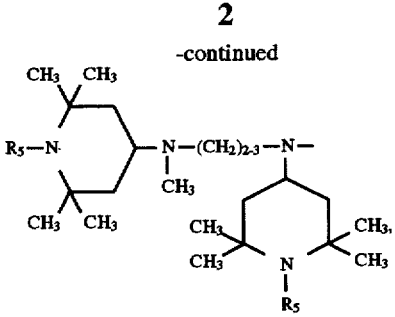

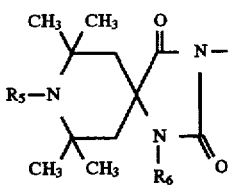

in which
$R_5$ is hydrogen, $C_1$–$C_8$alkyl, O⁻, OH, NO, $CH_2CN$, $C_1$–$C_{18}$alkoxy, $C_5$–$C_{12}$cycloalkoxy, $C_7$–$C_9$phenylalkyl either unsubstituted or substituted on the phenyl with 1, 2 or 3 $C_1$–$C_4$alkyls; or $C_1$–$C_8$acyl;

E is >CO, —$CH_2CH_2$—, —$CH_2CO$, —COCO— or —COCH$_2$CO—;

p is zero or 1 and, when p is zero, E is a —$CH_2$—$CH_2$— group;

$R_6$ is hydrogen, methyl or benzyl;

$R_4$ is hydrogen, $C_1$–$C_{18}$alkyl; $C_5$–$C_{12}$cycloalkyl, phenyl, $C_7$–$C_9$phenylalkyl either unsubstituted or substituted on the phenyl with 1, 2 or 3 $C_1$–$C_4$alkyls; $C_7$–$C_9$bicycloalkyl or one of the groups of formula (IIIa)–(IIIg)

$$R_7-O-R_8-, \quad (IIIa)$$

$$\overset{O}{\underset{\|}{(R_9-A-C)_q R_{10}-}}, \quad (IIIb)$$

$$R_{11}-\underset{\underset{R_{12}}{|}}{N}-COO-R_{13}-, \quad (IIIc)$$

(IIId)

(IIIe)

(IIIf)

(IIIg)

in which
$R_7$ is $C_1$–$C_{18}$alkyl, $C_5$–$C_{12}$cycloalkyl either unsubstituted or substituted with 1, 2 or 3 $C_1$–$C_4$alkyls; phenyl either unsubstituted or substituted with 1, 2 or 3 $C_1$–$C_4$alkyls or with $C_1$–$C_4$alkoxy; $C_7$–$C_9$phenylalkyl either unsubstituted or substituted on the phenyl with 1, 2 or 3 $C_1$–$C_4$alkyls; or a group of formula (IV)

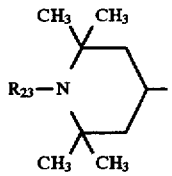

where $R_{23}$ has any one of the meanings given for $R_5$;

$R_8$ is $C_2$–$C_{12}$alkylene;

$R_9$ is $C_1$–$C_{18}$alkyl, $C_5$–$C_{12}$cycloalkyl either unsubstituted or substituted with 1, 2 or 3 $C_1$–$C_4$alkyls; phenyl either unsubstituted or substituted with 1, 2 or 3 $C_1$–$C_4$alkyls or with 1, 2 or 3 $C_1$–$C_4$alkoxy; $C_7$–$C_9$phenylalkyl either unsubstituted or substituted on the phenyl with 1, 2 or 3 $C_1$–$C_4$alkyls; tetrahydrofurfuryl or a group of formula (IV);

A is —O— or >N—$R_{24}$ where $R_{24}$ is hydrogen, $C_1$–$C_{18}$alkyl, phenyl, benzyl or a group of formula (IV);

q is 1, 2 or 3; when q is 1, $R_{10}$ is $C_2$–$C_{18}$alkylene; when q is 2, $R_{10}$ is $C_2$–$C_{20}$alkanetriyl, $C_5$–$C_7$cycloalkanetriyl or $C_7$–$C_9$bicycloalkanetriyl; and, when q is 3, $R_{10}$ is $C_3$–$C_6$alkanetetrayl;

$R_{11}$ and $R_{12}$, which may be identical or different, are as defined above for $R_9$ or

represents a heterocycle with 5–7 members;

$R_{13}$ is $C_2$–$C_{12}$alkylene;

$R_{14}$ is as defined for $R_9$;

$R_{15}$ is a direct linkage or $C_1$–$C_{18}$alkylene;

$R_{16}$ is hydrogen or $C_1$–$C_8$alkyl;

$R_{17}$ is $C_2$–$C_{18}$alkylene;

$R_{18}$ is without meaning or is —$CH_2$— or —$CH_2CH_2$—;

$R_{19}$ is hydrogen or methyl;

$R_{20}$ and $R_{21}$, which may be identical or different, are one of the groups of formula (IIa)–(IIc) or a group

or $R_{27}$—O— where $R_{25}$, $R_{26}$ and $R_{27}$, which may be identical or different, are as defined above for $R_9$ or

is a heterocycle with 5–7 members;

A' has one of the definitions of A;

$R_{22}$ is $C_2$–$C_{12}$alkylene;

$L_1$ has any one of the meanings given to $R_1$ or is a group $(R_{28})_3SiO$— where $R_{28}$ is $C_1$–$C_{18}$alkyl;

$L_2$ is hydrogen, Na, K, $C_1$–$C_8$alkyl, a group $(R_{28})_3Si$— with $R_{28}$ as defined above, or, when n is zero and $R_1$ and $L_1$ are $C_1$–$C_{18}$alkyl or phenyl, $L_2$ is also a group of formula (V)

and, when m+n is a number from 3 to 10, $L_1$ and $L_2$ together can also represent a direct linkage.

Each of G, $R_1$, $R_2$, $R_3$ and $R_4$ can have, in the individual repeating units of formula (I), the same meaning or different meanings and the various repeating units can have a random or block distribution.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy.

Examples of $C_5$–$C_{12}$cycloalkyl either unsubstituted or substituted with 1, 2 or 3 $C_1$–$C_4$alkyls are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl either unsubstituted or substituted with $C_1$–$C_4$alkyl is preferred.

Examples of $C_5$–$C_{12}$cycloalkoxy are cyclopentoxy, cyclohexoxy, cycloheptoxy, cyclooctoxy, cyclodecyloxy and cyclododecyloxy. Cyclopentoxy and cyclohexoxy are preferred.

Examples of $C_7$–$C_9$phenylalkyl either unsubstituted or substituted on the phenyl with 1, 2 or 3 $C_1$–$C_4$alkyls are benzyl, methylbenzyl, dimethylbenzyl, trimethylbenzyl, t-butylbenzyl and 2-phenylethyl. Benzyl is preferred.

Examples of $C_1$–$C_8$acyl are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

For $R_{10}$, when p is 1, representative examples of $C_2$–$C_{18}$alkylene are ethylene, ethylidene, propylene, propylidene, trimethylene, methyltrimethylene, tetramethylene, pentamethylene, hexylene, decamethylene and groups of formula

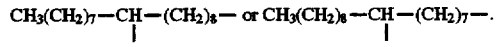

Examples of alkylene containing not more than 18 carbon atoms are methylene, ethylene, propylene, trimethylene, 2-methyltrimethylene, tetramethylene, pentamethylene, hexamethylene, octamethylene, decamethylene, undecamethylene, dodecamethylene, tetradecamethylene, hexadecamethylene and octadecamethylene. Trimethylene is preferred.

Examples of $C_7$–$C_9$bicycloalkyl are bicycloheptyl and decahydronaphthyl.

Examples of phenyl substituted with 1, 2 or 3 $C_1$–$C_4$alkyls or with 1, 2 or 3 $C_1$–$C_4$alkoxy are methylphenyl, dimethylphenyl, trimethylphenyl, isopropylphenyl, diisopropylphenyl, di-t-butylphenyl, methoxyphenyl, dimethoxyphenyl, ethoxyphenyl, propoxyphenyl, butoxyphenyl and di-t-butoxyphenyl.

For $R_{10}$, when p is 2, representative examples of $C_2$-$C_{20}$alkanetriyl are ethanetriyl, propanetriyl, butanetriyl or a group

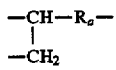

where $R_a$ is a linear or branched $C_3$-$C_{18}$alkanediyl such as trimethylene, butylene, pentylene, hexylene, octylene, decylene, dodecylene, tetradecylene, hexadecylene or octadecylene.

When $R_{10}$ is $C_5$-$C_7$cycloalkanetriyl or $C_7$-$C_9$bicycloalkanetriyl, representative examples are the groups

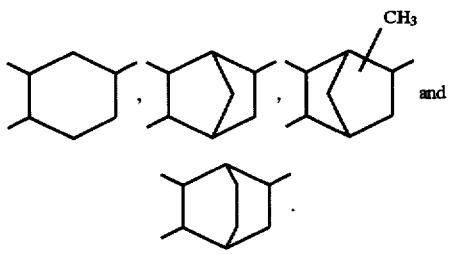

When $R_{10}$ is $C_3$-$C_6$alkanetetrayl, representative examples are propanetetrayl, butanetetrayl and pentanetetrayl.

Representative examples for

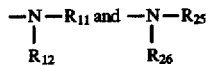

are 1-pyrrolidyl, 1-piperidyl and 4-morpholinyl. 4-Morpholinyl is preferred.

$R_5$ and $R_{23}$, which may be identical or different, are preferably independently of one another hydrogen, $C_1$-$C_4$alkyl, $C_1$-$C_{12}$alkoxy, $C_5$-$C_{12}$cycloalkoxy, benzyl either unsubstituted or substituted with 1, 2 or 3 $C_1$-$C_4$alkyls; or $C_1$-$C_4$acyl. Hydrogen and $C_1$-$C_4$alkyl, for example methyl, are particularly preferred.

The sum m+n may be, for example, also a number from 2 to 100, 4 to 100, 8 to 100, 2 to 70, 4 to 70 or 8 to 70. The variable n may also vary from 10 to 90%, e.g. 20 to 90% or 30 to 90%, of the sum m+n. Furthermore, the variable m may be for example a number from 5 to 50 or 10 to 50 and the variable n may be for example a number from 0 to 50, 5 to 50 or 10 to 50.

Some preferred meanings of $R_{27}$ are phenyl, tolyl, ethylphenyl, isopropylphenyl, di-t-butylphenyl, methoxyphenyl, ethoxyphenyl and di-t-butoxyphenyl.

Preferred compounds of formula (I) are those in which m+n is a number from 1 to 90 and n varies from zero to 90% of the sum m+n;

$R_1$ and $R_3$, which may be identical or different, are $C_1$-$C_8$alkyl, phenyl, $C_1$-$C_6$alkoxy or OH;

$R_2$ is $C_2$-$C_8$alkylene;

G is one of the groups of formula (IIa)–(IId);

E is >CO, —$CH_2CH_2$— or —$CH_2CO$—;

p is zero or 1 and, when p is zero, E is —$CH_2CH_2$—;

$R_6$ is hydrogen, methyl or benzyl;

$R_4$ is hydrogen, $C_1$-$C_{18}$alkyl, $C_5$-$C_8$cycloalkyl, phenyl, benzyl either unsubstituted or substituted with 1, 2 or 3 $C_1$-$C_4$alkyls; bicycloheptyl or one of the groups of formula (IIIa)–(IIIg) in which $R_7$ is $C_1$-$C_{12}$alkyl, $C_5$-$C_8$cycloalkyl either unsubstituted or substituted with 1, 2 or 3 $C_1$-$C_4$alkyls; benzyl either unsubstituted or substituted with 1, 2 or 3 $C_1$-$C_4$alkyls; phenyl either unsubstituted or substituted with 1, 2 or 3 $C_1$-$C_4$alkyls or with 1, 2 or 3 $C_1$-$C_4$alkoxy; or a group of formula (IV);

$R_8$ is $C_2$-$C_8$alkylene;

$R_9$ is $C_1$-$C_8$alkyl, $C_5$-$C_8$cycloalkyl either unsubstituted or substituted with 1, 2 or 3 $C_1$-$C_4$alkyls; phenyl either unsubstituted or substituted with 1, 2 or 3 $C_1$-$C_4$alkyls or with 1, 2 or 3 $C_1$-$C_4$alkoxy; benzyl either unsubstituted or substituted with 1, 2 or 3 $C_1$-$C_4$alkyls; tetrahydrofurfuryl or a group of formula (IV);

A is —O— or >N—$R_{24}$ where $R_{24}$ is hydrogen, $C_1$-$C_{12}$alkyl, phenyl, benzyl or a group of formula (IV);

q is 1, 2 or 3 and, when q is 1, $R_{10}$ is $C_2$-$C_{12}$alkylene; when q is 2, $R_{10}$ is $C_2$-$C_{16}$alkanetriyl, $C_6$-$C_7$cycloalkanetriyl or $C_7$-$C_9$bicycloalkanetriyl; and, when q is 3, $R_{10}$ is $C_3$-$C_4$alkanetetrayl;

$R_{11}$ and $R_{12}$, which may be identical or different, are as defined above for $R_9$ or together with the nitrogen atom to which they are bound, represent a 1-pyrrolidyl, 1-piperidyl or 4-morpholinyl group;

$R_{13}$ is $C_2$-$C_8$alkylene;

$R_{14}$ is as defined above for $R_9$;

$R_{15}$ is a direct linkage or $C_1$-$C_{12}$alkylene;

$R_{16}$ is hydrogen or $C_1$-$C_{12}$alkyl;

$R_{17}$ is $C_2$-$C_{12}$alkylene;

$R_{18}$ is —$CH_2$— or —$CH_2CH_2$—;

$R_{19}$ is hydrogen or methyl;

$R_{20}$ and $R_{21}$, which may be identical or different, are one of the groups of formula (IIa)–(IIc) or a group

or $R_{27}O$— in which $R_{25}$, $R_{26}$ and $R_{27}$, which may be identical or different, are as defined above for $R_9$, or $R_{25}$ and $R_{26}$ together with the nitrogen atom to which they are bound represent a 1-pyrrolidyl, 1-piperidyl or 4-morpholinyl group;

A' has one of the definitions of A;

$R_{22}$ is $C_2$-$C_8$alkylene;

$L_1$ has any one of the meanings given to $R_1$ or is a group $(R_{28})_3SiO$— where $R_{28}$ is $C_1$-$C_8$alkyl;

$L_2$ is hydrogen, $C_1$-$C_8$alkyl, a group $(R_{28})_3Si$— with $R_{28}$ as defined above, or, when n is zero and $R_1$ and $L_1$ are $C_1$-$C_8$alkyl or phenyl, $L_2$ is also a group of formula (V), and, when m+n is a number from 3 to 10, $L_1$ and $L_2$ together also form a direct linkage.

Particularly preferred compounds of formula (I) are those in which m+n is a number from 1 to 80 and n varies from zero to 90% of the sum m+n;

$R_1$ and $R_3$, which may be identical or different, are $C_1$-$C_4$alkyl, $C_1$-$C_4$alkoxy or OH;

$R_2$ is $C_2$-$C_6$alkylene;

G is one of the groups of formula (IIa)–(IId);

E is >CO or —$CH_2CH_2$—;

p is zero or 1 and, when p is zero, E is —$CH_2CH_2$—;

$R_6$ is hydrogen or methyl;

$R_4$ is hydrogen, $C_1$-$C_{18}$alkyl, cyclohexyl, cycloheptyl, benzyl or one of the groups of formula (IIIa)–(IIIg) in which $R_7$ is $C_1$-$C_8$alkyl, cyclohexyl either unsubstituted or substituted with 1, 2 or 3 $C_1$-$C_4$alkyls; phenyl, tolyl, ethylphenyl, di-t-butylphenyl, methoxyphenyl, benzyl or a group of formula (IV);

$R_8$ is $C_2$-$C_6$alkylene;

$R_9$ is $C_1$-$C_4$alkyl, cyclohexyl either unsubstituted or substituted with 1, 2 or 3 $C_1$-$C_4$alkyls; phenyl, benzyl, tetrahydrofurfuryl or a group of formula (IV);

A is —O— or >N—$R_{24}$ where $R_{24}$ is hydrogen, $C_1$–$C_{10}$alkyl, benzyl or a group of formula (IV);

q is 1, 2 or 3 and, when q is 1, $R_{10}$ is $C_2$–$C_{12}$alkylene; when q is 2, $R_{10}$ is $C_2$–$C_{14}$alkanetriyl, cyclohexanetriyl or bicycloheptanetriyl; and, when q is 3, $R_{10}$ is propanetetrayl;

$R_{11}$ and $R_{12}$, which may be identical or different, are as defined above for $R_9$ or together with the nitrogen atom to which they are bound represent the 4-morpholinyl group;

$R_{13}$ is $C_2$–$C_6$alkylene;

$R_{14}$ is as defined above for $R_9$;

$R_{15}$ is a direct linkage or $C_1$–$C_8$alkylene;

$R_{16}$ is hydrogen or $C_1$–$C_8$alkyl;

$R_{17}$ is $C_3$–$C_6$alkylene;

$R_{18}$ is methylene;

$R_{19}$ is hydrogen or methyl;

$R_{20}$ and $R_{21}$, which may be identical or different, are one of the groups of formula (IIa)–(IIc) or group

or $R_{27}$O— in which $R_{25}$, $R_{26}$ and $R_{27}$, which may be identical or different, are as defined above for $R_9$, or $R_{25}$ and $R_{26}$ together with the nitrogen atom to which they are bound represent a 4-morpholinyl group or $R_{27}$ is also tolyl, ethylphenyl, di-t-butylphenyl or methoxyphenyl;

A' has one of the definitions of A;

$R_{22}$ is $C_2$–$C_6$alkylene;

$L_1$ has any one of the meanings given to $R_1$ or is a group $(R_{28})_3$SiO— where $R_{28}$ is $C_1$–$C_4$alkyl;

$L_2$ is hydrogen, $C_1$–$C_4$alkyl, a group $(R_{28})_3$Si— with $R_{28}$ as defined above, or, when n is zero and $R_1$ and $L_1$ are $C_1$–$C_4$alkyl, $L_2$ is also a group of formula (V), and, when m+n is a number from 3 to 10, $L_1$ and $L_2$ together can also represent a direct linkage.

Compounds of formula (I) of especial interest are those in which m+n is a number from 1 to 70 and n varies from zero to 90% of the sum m+n;

$R_1$ and $R_3$, which may be identical or different, are methyl, ethyl, methoxy or OH;

$R_2$ is $C_2$–$C_3$alkylene;

G is one of the groups (IIa)–(IId);

E is >CO or —$CH_2CH_2$—;

p is 1;

$R_6$ is hydrogen or methyl;

$R_4$ is hydrogen, $C_1$–$C_{18}$alkyl, cyclohexyl, one of the groups of formula (IIIa), (IIIb), (IIIc), (IIId) or (IIIg) in which $R_7$ is $C_1$–$C_4$alkyl, phenyl, tolyl, di-t-butylphenyl, benzyl or a group of formula (IV);

$R_8$ is $C_2$–$C_3$alkylene;

$R_9$ is $C_1$–$C_4$alkyl, cyclohexyl, benzyl or a group of formula (IV);

A is —O— or

—N—$R_{24}$ where $R_{24}$ is hydrogen, $C_1$–$C_8$alkyl, benzyl or a group of formula (IV);

q is 1 or 2 and, when q is 1, $R_{10}$ is $C_2$–$C_{10}$alkylene; and, when q is 2, $R_{10}$ is $C_2$–$C_{14}$alkanetriyl;

$R_{11}$ and $R_{12}$, which may be identical or different, are as defined above for $R_9$;

$R_{13}$ is $C_2$–$C_3$alkylene;

$R_{14}$ is as defined above for $R_9$;

$R_{15}$ is $C_2$–$C_3$alkylene;

$R_{20}$ and $R_{21}$, which may be identical or different, are one of the groups of formula (IIa)–(IIc) or a group

or $R_{27}$O— in which $R_{25}$, $R_{26}$ and $R_{27}$, which may be identical or different, are as defined above for $R_9$, or $R_{27}$ can also be phenyl or di-t-butylphenyl;

A' has one of the definitions of A;

$R_{22}$ is $C_2$–$C_3$alkylene;

$L_1$ has any one of the meanings given to $R_1$ or is a group $(R_{28})_3$SiO— where $R_{28}$ is methyl;

$L_2$ is hydrogen, methyl, ethyl, a group $(R_{28})_3$Si— with $R_{28}$ as defined above, or, when n is zero and $R_1$ and $L_1$ are methyl, $L_2$ is also a group of formula (V), and, when m+n is a number from 3 to 10, $L_1$ and $L_2$ together can also represent a direct linkage.

Compounds of formula (I) of particular interest are those in which m+n is a number from 1 to 60 and n varies from zero to 90% of the sum m+n;

$R_1$ and $R_3$, which may be identical or different, are methyl, methoxy or OH;

$R_2$ is trimethylene;

G is one of the groups of formula (IIa), (IIc) or (IId);

$R_5$ is hydrogen or methyl;

E is >CO and p is 1;

$R_6$ is hydrogen;

$R_4$ is hydrogen, $C_1$–$C_{18}$alkyl, one of the groups of formula (IIIa), (IIIb), (IIIc) or (IIIg);

$R_7$ is a group of formula (IV);

$R_8$ is trimethylene;

$R_9$ is a group of formula (IV);

$R_{23}$ is hydrogen or methyl;

A is —O— or >N—$R_{24}$ where $R_{24}$ is hydrogen, $C_1$–$C_4$alkyl or a group of formula (IV);

q is 1 or 2 and, when q is 1, $R_{10}$ is $C_2$–$C_{10}$alkylene; and, when q is 2, $R_{10}$ is $C_2$–$C_{14}$alkanetriyl;

$R_{11}$ and $R_{12}$, which may be identical or different, are as defined above for $R_9$;

$R_{13}$ is trimethylene;

$R_{20}$ and $R_{21}$, which may be identical or different, are a group

in which $R_{25}$ and $R_{26}$, which may be identical or different, are $C_1$–$C_4$alkyl or a group of formula (IV);

A' has one of the definitions of A;

$R_{22}$ is trimethylene;

$L_1$ has any one of the meanings given to $R_1$ or is a group $(R_{28})_3$SiO— where $R_{28}$ is methyl;

$L_2$ is hydrogen, methyl, a group $(R_{28})_3$Si— with $R_{28}$ as defined above, or, when n is zero and $R_1$ and $L_1$ are methyl, $L_2$ is also a group of formula (V), and, when m+n is a number from 3 to 10, $L_1$ and $L_2$ together can also represent a direct linkage.

The compounds of the present invention can be prepared in analogy to various conventional methods.

Some examples for the preparation are indicated below.

Method 1

When m is 1 and n is zero, $R_1$ is $C_1$–$C_{18}$alkyl, $C_1$–$C_8$alkoxy or phenyl, $L_1$ is $C_1$–$C_{18}$alkyl, $C_1$–$C_8$alkoxy, phenyl or a group $(R_{28})_3$SiO— and $L_2$ is $C_1$–$C_8$alkyl or a group $(R_{28})_3Si-$, or, when $L_1$ and $R_1$ are $C_1-C_{18}$alkyl or phenyl, $L_2$ also is a group $$L_1-\underset{\underset{G}{\overset{R_1}{|}}}{\overset{R_1}{\overset{|}{Si}}}-,\quad (5)$$

the compounds of formula (I) are preferably be prepared according to scheme 1, by reacting an alkene capable of forming a group —$R_2$—G as defined above, with a silane of formula (VI).

Scheme 1

$$L_1-\underset{\underset{H}{\overset{R_1}{|}}}{\overset{R_1}{\overset{|}{Si}}}-O-L_2 + \overset{\diagdown}{\diagup}C=C\overset{\diagup}{\diagdown} \longrightarrow L_1-\underset{\underset{G}{\overset{R_2}{|}}}{\overset{R_1}{\overset{|}{Si}}}-O-L_2$$

(VI)  (VII)

The hydrosilylation reaction (Speier; J.A.C.S. 79, 974, 1957) is conveniently carried out in the presence of catalytic amounts of Pd, Pt, Rh or their derivatives, preferably complexes of Pt and Rh, in particular $H_2PtCl_6$ and the complex $PtCl_2(Ph-CH=CH_2)_2$, without solvent or in an inert solvent such as, for example, tetrahydrofuran, dioxane, hexane, heptane, cyclohexane, toluene, xylene, at temperatures between e.g. 60° C. and 150° C., preferably between 80° C. and 130° C.

Method 2

By complete or partial hydrolysis of the compounds of formula (VII), containing at least one alkoxy group bound to a silicon atom, it is possible to prepare the corresponding silanol compounds from which, by a condensation reaction, the corresponding compounds of formula (I) with m at least 2 and n≠zero is obtained.

The hydrolysis and condensation reactions are preferably effected simultaneously employing the conditions already described in U.S. Pat. No. 4,946,880 and U.S. Pat. No. 5,219,905.

Method 3

When m is at least 2 and n is different from zero, the compounds of formula (I) can be prepared, for examples, by hydrolysis/condensation of mixtures, in the appropriate proportions, of compounds of formula (VII) and of compounds of formula (VIII) or (IX)

$$R_{29}-\underset{\underset{R_4}{|}}{\overset{R_3}{\overset{|}{Si}}}-R_{29}, \quad (VIII)$$

$$\left[\underset{\underset{R_4}{|}}{\overset{R_3}{\overset{|}{Si}}}-O\right]_r \quad (IX)$$

in which $R_3$ and $R_4$ are as defined above. $R_{29}$ is $C_1-C_8$alkoxy and r is 3 or 4, if desired in the presence of suitable amounts of disiloxane $[(R_{28})_3Si]_2O$ as chain terminator, under the conditions stated in Method 2.

The compounds of formula (VIII) or (IX) can be prepared, for example, from the corresponding alkenes with a silane of formula (X) or of formula (XI)

$$R_{29}-\underset{\underset{H}{|}}{\overset{R_3}{\overset{|}{Si}}}-R_{29}, \quad (X)$$

$$\left[\underset{\underset{H}{|}}{\overset{R_3}{\overset{|}{Si}}}-O\right]_r \quad (XI)$$

with $R_3$ and $R_{29}$ and r as defined above, under the conditions stated in Method 1.

Method 4

Compounds of formula (I) with m at least 2 and with n=zero, or different from zero, when $R_1$ and $R_3$ are identical, can also be prepared, for example, by reacting a compound of formula (XII)

$$L_1\!-\!\!\left(\underset{\underset{H}{|}}{\overset{R_1}{\overset{|}{Si}}}-O\right)_{\!\!m+n}\!\!\!-L_2 \quad (XII)$$

($R_1=R_3$ for n≠zero)

where $R_1$, $R_4$, $L_1$, $L_2$, m and n are as defined above, with appropriate amounts of alkene capable of forming the groups —$R_2$—G and $R_4$ as defined above, as described in Method 1 or as stated in EP-A-343 717 and EP-A-388 321.

When $R_1$ and $L_1$ are OH, ONa or OK and $L_2$ is hydrogen, Na or K, the compounds of formula (I) can be prepared in accordance with the above mentioned method by further acidic or basic hydrolysis of the intermediate of formula (I) where $L_1$ and $R_1$ are methoxy and $L_2$ is methyl. The acidic hydrolysis may be carded out, for example, by using an aqueous solution of hydrochloric acid. The basic hydrolysis may be carried out, for example, by using a suitable aqueous basic solution such as sodium hydroxide, when $L_1$ and $R_1$ are ONa and $L_2$ is Na, or potassium hydroxide, when $L_1$ and $R_1$ are OK and $L_2$ is K.

As mentioned at the outset, the compounds of formula (I) are very effective for improving the light, heat and oxidation resistance of organic materials, especially synthetic polymers and copolymers, and are particularly suitable for stabilizing polypropylene fibres on account of their great resistance to volatilization.

Examples of organic materials that can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and mines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6,6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably 0.05 to 1%.

In general, the compounds of the formula (I) can be added to the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the mixtures of the compounds of the formula (I) with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methyl-undec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α- methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O—, N— and S—benzyl compounds, for example 3,5,3',5'-tetra-tert-butyl-4,4'-dihydroxy-dibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenylacetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, Bis[4-(1',3'-dimethylbutyl) phenyl]amine, tert-octylated N-phenyl-1-naphthylamine, a mixture of mono- and dialkylated tert-butyl/tert-octyldiphenylmines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-($\alpha,\alpha$-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-$\beta$-methyl-p-methoxy-cinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered mines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octyl-amino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis-(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cyclo-undecyl-1-oxa-3,8-diaza-4-oxospiro[4,5]decane and epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4- dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, mines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The compounds of the formula (1) can also be used as stabilisers, especially as light stabilisers, for almost all materials known in the art of photographic reproduction and other reproduction techniques as e.g. described in Research Disclosure 1990, 31429 (page 474 to 480).

For better illustration of the present invention, some examples of preparation and of use of the compounds of formula (I) will be given. The compounds of Examples 1 to 3 relate to a particularly preferred embodiment of the present invention.

EXAMPLE 1

Preparation of a Polysiloxane of the Formula

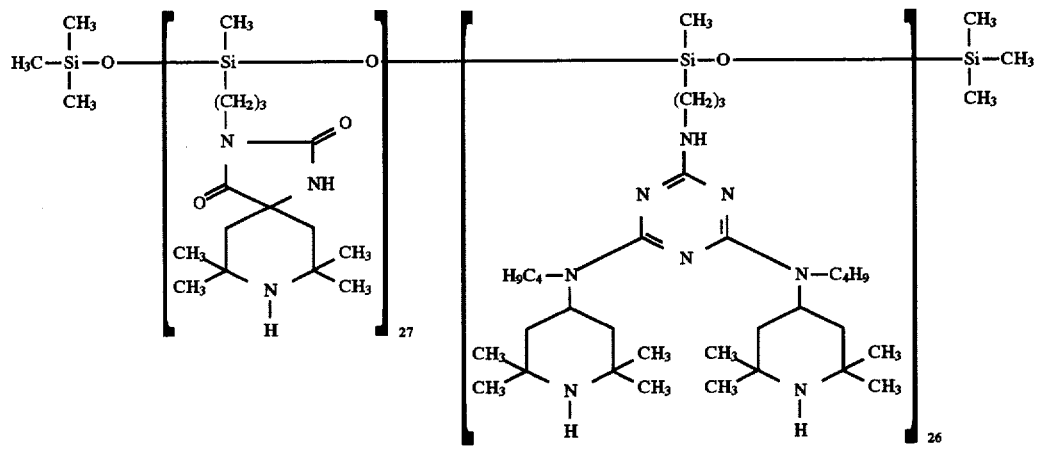

43.3 g (77.8 mmol) of 2-allylamino-4,6-bis[N-(2,2,6,6-tetramethyl-4-piperidyl)butylamino]-1,3,5-triazine are dissolved in 60 ml of xylene and 2 mg of $PtCl_2(styrene)_2$ are added. The solution is heated to 140° C. and, while stirring, a solution of 10 g (3 mmol) of trimethylsilyl terminated polymethylhydrosiloxane (having 53 Si-H units) in 150 ml of xylene is slowly added. The reaction is maintained at 140° C. for 3 hours. The temperature is lowered to 70° C. and, still with stirring, 21.2 g (87 mmol) of 3-allyl-7,7,9,9-tetramethyl-1,3,8-triaza-spiro[4.5]decane-2,4-dione and a further 2 mg of $PtCl_2(styrene)_2$ are added. The mixture is heated at 140° C. for 8 hours with stirring and the solvent and the excess reactant are removed by vacuum distillation (140° C./0.1 mbar). A very viscous resinous product is obtained, NMR and IR analysis of which confirms the expected structure.

Using the procedure analogous to that described in Example 1, 7.3 g (30 mmol) of 3-allyl-7,7,9,9-tetramethyl-1,3,8-triazaspiro[4.5]decane-2,4-dione are reacted with 10 g (3 mmol) of trimethylsilyl terminated polymethylhydrosiloxane (having 53 Si-H units) and with 15 g (133.9 mmol) of 1-octene in the presence of 4 mg of $PtCl_2(styrene)_2$ in xylene. After removing the solvent and the excess of 1-octene by vacuum distillation (140° C./1 mbar), a viscous oil product is obtained, NMR and IR analysis of which confirms the indicated structure.

EXAMPLE 2

Preparation of a Polysiloxane of the Formula

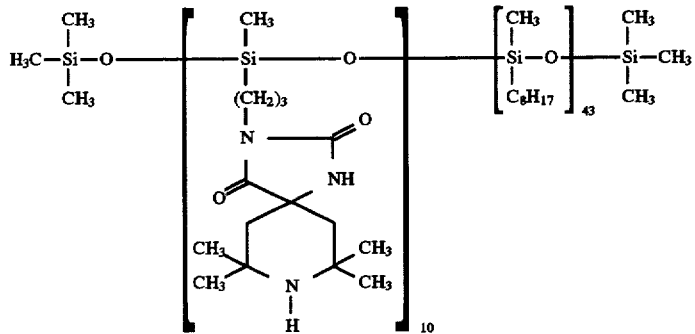

EXAMPLE 3

Preparation of a Polysiloxane of the Formula

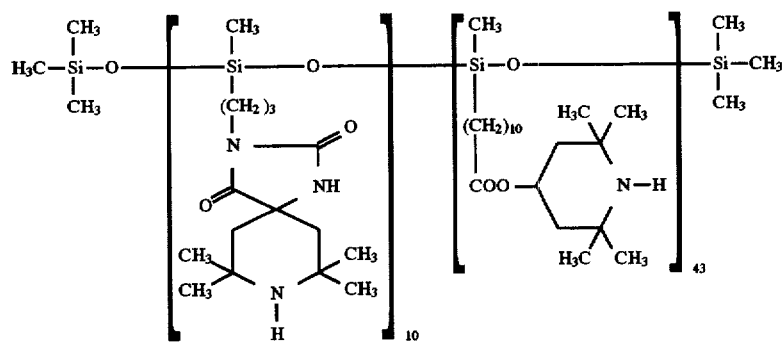

Using the procedure analogous to that described in Example 1, 41.7 g (129 mmol) of 2,2,6,6-tetramethyl-4-piperidyl ester of 10-undecenoic acid are reacted with 10 g (3 mmol) of trimethylsilyl terminated polymethylhydrosiloxane (having 53 Si-H units) and with 8.7 g (36 mmol) of 3-allyl-7,7,9,9-tetramethyl-1,3,8-triazaspiro[4,5]decane-2,4-dione in the presence of 6 mg of $PtCl_2(styrene)_2$ in xylene.

After washing with an aqueous solution of 0.2N HCl, with an aqueous solution of 5% NaOH (% w/v) and with water, the organic phase is dried under $Na_2SO_4$, filtered and evaporated under vacuum (80° C./1 mbar).

A very viscous resinous product is obtained, NMR and IR analysis of which confirms the expected structure.

EXAMPLE 4

Light-stabilizing Action in Polypropylene Fibres 2.5 g of the product shown in Table 1, 1 g of tris(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder having a melt index=12 g/10 min (measured at 230° C. and 2.16 kg).

The mixtures are extruded at 200°–230° to obtain polymer granules which are then convened into fibres using a pilot-type apparatus (®Leonard-Sumirago (VA) Italy) and operating under the following conditions:

extruder temperature: 230°–245° C.
head temperature: 255°–260° C.
draw ratio: 1:3.5
linear density: 11 dtex per filament The fibres prepared in this way are exposed, after mounting on white cardboard, in a 65WR Weather-O-Meter (ASTM D2565-85) with a black-panel temperature of 63° C.

For samples taken after various times of exposure to the light, the residual tenacity is measured using a constant-speed tensometer, and the exposure time in hours needed to halve the initial tenacity ($T_{50}$) is then calculated.

For purposes of comparison, fibres prepared under the same conditions as stated above, but without adding the stabilizers of the present invention, are also exposed. The results are shown in Table 1.

TABLE 1

| Stabilizer | $T_{50}$ (hours) |
|---|---|
| without stabilizer | 220 |
| compound of Example 1 | >1000 |

What is claimed is:
1. A compound of formula (I)

$$L_1 - \left( \begin{array}{c} R_1 \\ | \\ Si - O \\ | \\ R_2 \\ | \\ G \end{array} \right)_m \left( \begin{array}{c} R_3 \\ | \\ Si - O \\ | \\ R_4 \end{array} \right)_n L_2 \quad (I)$$

in which m+n is a number from 1 to 100 and n varies from zero to 90% of the sum of m+n;

$R_1$ and $R_3$, which may be identical or different, are $C_1-C_{18}$alkyl, phenyl, $C_1-C_8$alkoxy, OH, ONa or OK;

$R_2$ is $C_2-C_{12}$alkylene;

G is one of the groups of formula (IIa)–(IId)

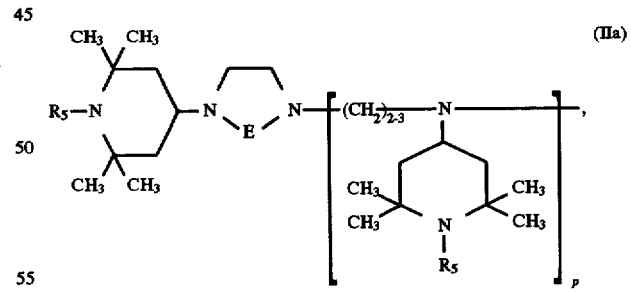

(IIa)

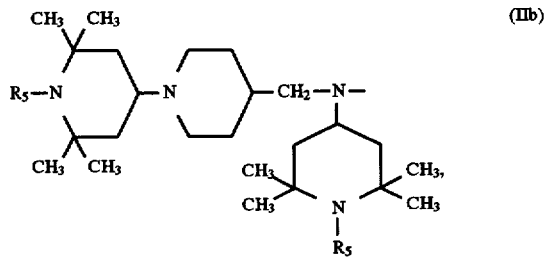

(IIb)

-continued

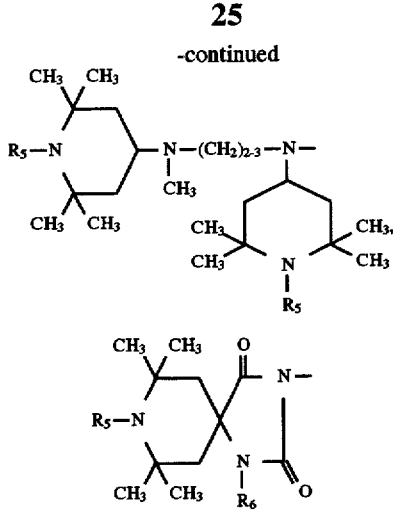
(IIc)

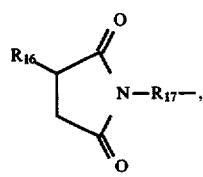
(IId)

in which

R$_5$ is hydrogen, C$_1$–C$_8$alkyl, O$^-$, OH, NO, CH$_2$CN, C$_1$–C$_{18}$alkoxy, C$_5$–C$_{12}$cycloalkoxy, C$_7$–C$_9$phenylalkyl either unsubstituted or substituted on the phenyl with 1, 2 or 3 C$_1$–C$_4$alkyls; or C$_1$–C$_8$acyl;

E is —CO—, —CH$_2$CH$_2$—, —CH$_2$CO, —COCO— or —COCH$_2$CO—;

p is zero or 1 and, when p is zero, E is a —CH$_2$—CH$_2$— group;

R$_6$ is hydrogen, methyl or benzyl;

R$_4$ as hydrogen, C$_1$–C$_{18}$alkyl; C$_5$–C$_{12}$cycloalkyl, phenyl, C$_7$–C$_9$phenylalkyl either unsubstituted or substituted on the phenyl with 1, 2 or 3 C$_1$–C$_4$alkyls; C$_7$–C$_9$bicycloalkyl or one of the groups of formula (IIIa)–(IIIg)

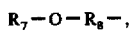 (IIIa)

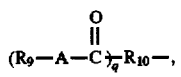 (IIIb)

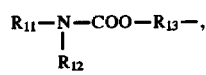 (IIIc)

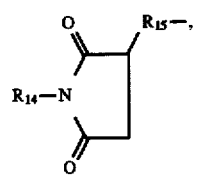 (IIId)

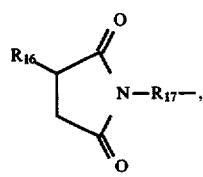 (IIIe)

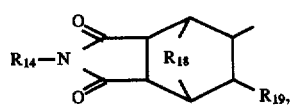 (IIIf)

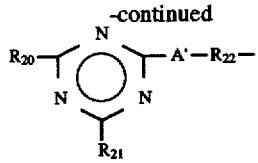 (IIIg)

in which

R$_7$ is C$_1$–C$_{18}$alkyl, C$_5$–C$_{12}$cycloalkyl either unsubstituted or substituted with 1, 2 or 3 C$_1$–C$_4$alkyls; phenyl either unsubstituted or substituted with 1, 2 or 3 C$_1$–C$_4$alkyls or with C$_1$–C$_4$alkoxy; C$_7$–C$_9$phenylalkyl either unsubstituted or substituted on the phenyl with 1, 2 or 3 C$_1$–C$_4$alkyls; or a group of formula (IV)

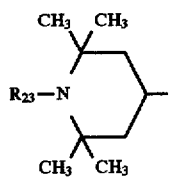 (IV)

where

R$_{23}$ has any one of the meanings given for R$_5$;

R$_8$ is C$_2$–C$_{12}$alkylene;

R$_9$ is C$_1$–C$_{18}$alkyl, C$_5$–C$_{12}$cycloalkyl either unsubstituted or substituted with 1, 2 or 3 C$_1$–C$_4$alkyls; phenyl either unsubstituted or substituted with 1, 2 or 3 C$_1$–C$_4$alkyls or with 1, 2 or 3 C$_1$–C$_4$alkoxy; C$_7$–C$_9$phenylalkyl either unsubstituted or substituted on the phenyl with 1, 2 or 3 C$_1$–C$_4$alkyls; tetrahydrofurfuryl or a group of formula (IV);

A is —O— or —NR$_{24}$— where R$_{24}$ is hydrogen, C$_1$–C$_{18}$alkyl, phenyl, benzyl or a group of formula (IV);

q is 1, 2 or 3; when q is 1, R$_{10}$ is C$_2$–C$_{18}$alkylene; when q is 2, R$_{10}$ is C$_2$–C$_{20}$alkanetriyl, C$_5$–C$_7$cycloalkanetriyl or C$_7$–C$_9$bicycloalkanetriyl; and, when q is 3, R$_{10}$ is C$_3$–C$_6$alkanetetrayl;

R$_{11}$ and R$_{12}$, which may be identical or different, are as defined above for R$_9$ or

represents a heterocycle with 5–7 members;

R$_{13}$ is C$_2$–C$_{12}$alkylene;

R$_{14}$ is as defined for R$_9$;

R$_{15}$ is a direct linkage or C$_1$–C$_{18}$alkylene;

R$_{16}$ is hydrogen or C$_1$–C$_{18}$alkyl;

R$_{17}$ is C$_2$–C$_{18}$alkylene;

R$_{18}$ is without meaning or is —CH$_2$— or —CH$_2$CH$_2$—;

R$_{19}$ is hydrogen or methyl;

R$_{20}$ and R$_{21}$, which may be identical or different, are one of the groups of formula (IIa)–(IIc) or a group

or R$_{27}$—O— where R$_{25}$, R$_{26}$ and R$_{27}$, which may be identical or different, are as defined above for R$_9$ or

is a heterocycle with 5–7 members;
A' has one of the definitions of A;
$R_{22}$ is $C_2$–$C_{12}$alkylene;
$L_1$ has any one of the meanings given to $R_1$ or is a group $(R_{28})_3$SiO— where $R_{28}$ is $C_1$–$C_{18}$alkyl;
$L_2$ is hydrogen, Na, K, $C_1$–$C_8$alkyl, a group $(R_{28})_3$Si— with $R_{28}$ as defined above, or, when is zero and $R_1$ and $L_1$ are $C_1$–$C_{18}$alkyl or phenyl, $L_2$ is also a group of formula (V)

and, when m+n is a number from 3 to 10, $L_1$ and $L_2$ together can also represent a direct linkage.

2. A compound of formula (I) according to claim 1, in which m+n is a number from 1 to 90 and n varies from zero to 90% of the sum m+n;

$R_1$ and $R_3$, which may be identical or different, are $C_1$–$C_8$alkyl, phenyl, $C_1$–$C_6$alkoxy or OH;

$R_2$ is $C_2$–$C_8$alkylene;

G is one of the groups of formula (IIa)–(IId);

E is —CO—, —CH$_2$CH$_2$— or —CH$_2$CO—;

p is zero or 1 and, when p is zero, E is —CH$_2$CH$_2$—;

$R_6$ is hydrogen, methyl or benzyl;

$R_4$ is hydrogen, $C_1$–$C_{18}$alkyl, $C_5$–$C_8$cycloalkyl, phenyl, benzyl either unsubstituted or substituted with 1, 2 or 3 $C_1$–$C_4$alkyls; bicycloheptyl or one of the groups of formula (IIIa)–(IIIg) in which $R_7$ is $C_1$–$C_{12}$alkyl, $C_5$–$C_8$cycloalkyl either unsubstituted or substituted with 1, 2 or 3 $C_1$–$C_4$alkyls; benzyl either unsubstituted or substituted with 1, 2 or 3 $C_1$–$C_4$alkyls; phenyl either unsubstituted or substituted with 1, 2 or 3 $C_1$–$C_4$alkyls or with 1, 2 or 3 $C_1$–$C_4$alkoxy; or a group of formula (IV);

$R_8$ is $C_2$–$C_8$alkylene;

$R_9$ is $C_1$–$C_8$alkyl, $C_5$–$C_8$cycloalkyl either unsubstituted or substituted with 1, 2 or 3 $C_1$–$C_4$alkyls; phenyl either unsubstituted or substituted with 1, 2 or 3 $C_1$–$C_4$alkyls or with 1, 2 or 3 $C_1$–$C_4$alkoxy; benzyl either unsubstituted or substituted with 1, 2 or 3 $C_1$–$C_4$alkyls; tetrahydrofurfuryl or a group of formula (IV);

A is —O— or —NR$_{24}$— where $R_{24}$ is hydrogen, $C_1$–$C_{12}$alkyl, phenyl, benzyl or a group of formula (IV);

q is 1, 2 or 3 and, when q is 1, $R_{10}$ is $C_{2-12}$alkylene; when q is 2, $R_{10}$ is $C_2$–$C_{16}$alkanetriyl, $C_6$–$C_7$cycloalkanetriyl or $C_7$–$C_9$bicycloalkanetriyl; and, when q is 3, $R_{10}$ is $C_3$–$C_4$alkanetetrayl;

$R_{11}$ and $R_{12}$, which may be identical or different, are as defined above for $R_9$ or together with the nitrogen atom to which they are bound, represent a 1-pyrrolidyl, 1-piperidyl or 4-morpholinyl group;

$R_{13}$ is $C_2$–$C_8$alkylene;

$R_{14}$ is as defined above for $R_9$;

$R_{15}$ is a direct linkage or $C_1$–$C_{12}$alkylene;

$R_{16}$ is hydrogen or $C_1$–$C_{12}$alkyl;

$R_{17}$ is $C_2$–$C_{12}$alkylene;

$R_{18}$ is —CH$_2$— or —CH$_2$CH$_2$—;

$R_{19}$ is hydrogen or methyl;

$R_{20}$ and $R_{21}$, which may be identical or different, are one of the groups of formula (IIa)–(IIc) or a group

or $R_{27}$O— in which $R_{25}$, $R_{26}$ and $R_{27}$, which may be identical or different, are as defined above for $R_9$, or $R_{25}$ and $R_{26}$ together with the nitrogen atom to which they are bound represent a 1-pyrrolidyl, 1-piperidyl or 4-morpholinyl group;

A' has one of the definitions of A;

$R_{22}$ is $C_2$–$C_8$alkylene;

$L_1$ has any one of the meanings given to $R_1$ or is a group $(R_{28})_3$SiO— where $R_{28}$ is $C_1$–$C_8$alkyl;

$L_2$ is hydrogen, $C_1$–$C_8$alkyl, a group $(R_{28})_3$Si— with $R_{28}$ as defined above, or, when n is zero and $R_1$ and $L_1$ are $C_1$–$C_8$alkyl or phenyl, $L_2$ is also a group of formula (V), and, when m+n is a number from 3 to 10, $L_1$ and $L_2$ together also form a direct linkage.

3. A compound of formula (I) according to claim 1, in which m+n is a number from 1 to 80 and n varies from zero to 90% of the sum m+n;

$R_1$ and $R_3$, which may be identical or different, are $C_1$–$C_4$alkyl, $C_1$–$C_4$alkoxy or OH;

$R_2$ is $C_2$–$C_6$alkylene;

G is one of the groups of formula (IIa)–(IId);

E is —CO— or —CH$_2$CH$_2$—;

p is zero or 1 and, when p is zero, E is —CH$_2$CH$_2$—;

$R_6$ is hydrogen or methyl;

$R_4$ is hydrogen, $C_1$–$C_{18}$alkyl, cyclohexyl, cycloheptyl, benzyl or one of the groups of formula (IIIa)–(IIIg) in which $R_7$ is $C_1$–$C_8$alkyl, cyclohexyl either unsubstituted or substituted with 1, 2 or 3 $C_1$–$C_4$alkyls; phenyl, tolyl, ethylphenyl, di-t-butylphenyl, methoxyphenyl, benzyl or a group of formula (IV);

$R_8$ is $C_2$–$C_6$alkylene;

$R_9$ is $C_1$–$C_4$alkyl, cyclohexyl either unsubstituted or substituted with 1, 2 or 3 $C_1$–$C_4$alkyls; phenyl, benzyl, tetrahydrofurfuryl or a group of formula (IV);

A is —O— or —NR$_{24}$— where $R_{24}$ is hydrogen, $C_1$–$C_{10}$alkyl, benzyl or a group of formula (IV);

q is 1, 2 or 3 and, when q is 1, $R_{10}$ is $C_2$–$C_{12}$alkylene; when q is 2, $R_{10}$ is $C_2$–$C_{14}$alkanetriyl, cyclohexanetriyl or bicycloheptanetriyl; and, when q is 3, $R_{10}$ is propanetetrayl;

$R_{11}$ and $R_{12}$, which may be identical or different, are as defined above for $R_9$ or together with the nitrogen atom to which they are bound represent the 4-morpholinyl group;

$R_{13}$ is $C_2$–$C_6$alkylene;

$R_{14}$ is as defined above for $R_9$;

$R_{15}$ is a direct linkage or $C_1$–$C_8$alkylene;

$R_{16}$ is hydrogen or $C_1$–$C_8$alkyl;

$R_{17}$ is $C_3$–$C_6$alkylene;

$R_{18}$ is methylene;

$R_{19}$ is hydrogen or methyl;

$R_{20}$ and $R_{21}$, which may be identical or different, are one of the groups of formula (IIa)–(IIc) or a group

or $R_{27}O$— in which $R_{25}$, $R_{26}$ and $R_{27}$, which may be identical or different, are as defined above for $R_9$, or $R_{25}$ and $R_{26}$ together with the nitrogen atom to which they are bound represent a 4-morpholinyl group or $R_{27}$ is also tolyl, ethylphenyl, di-t-butylphenyl or methoxyphenyl;

A' has one of the definitions of A;

$R_{22}$ is $C_2$–$C_6$alkylene;

$L_1$ has any one of the meanings given to $R_1$ or is a group $(R_{28})_3SiO$— where $R_{28}$ is $C_1$–$C_4$alkyl;

$L_2$ is hydrogen, $C_1$–$C_4$alkyl, a group $(R_{28})_3Si$— with $R_{28}$ as defined above, or, when n is zero and $R_1$ and $L_1$ are $C_1$–$C_4$alkyl, $L_2$ is also a group of formula (V), and, when m+n is a number from 3 to 10, $L_1$ and $L_2$ together can also represent a direct linkage.

4. A compound of formula (I) according to claim 1, in which m+n is a number from 1 to 70 and n varies from zero to 90% of the sum m+n;

$R_1$ and $R_3$, which may be identical or different, are methyl, ethyl, methoxy or OH;

$R_2$ is $C_2$–$C_3$alkylene;

G is one of the groups (IIa)–(IId);

E is —CO— or —CH$_2$CH$_2$—;

p is 1;

$R_6$ is hydrogen or methyl;

$R_4$ is hydrogen, $C_1$–$C_{18}$alkyl, cyclohexyl, one of the groups of formula (IIIa), (IIIb), (IIIc), (IIId) or (IIIg) in which $R_7$ is $C_1$–$C_4$alkyl, phenyl, tolyl, di-t-butylphenyl, benzyl or a group of formula (IV);

$R_8$ is $C_2$–$C_3$alkylene;

$R_9$ is $C_1$–$C_4$alkyl, cyclohexyl, benzyl or a group of formula (IV);

A is —O— or

where $R_{24}$ is hydrogen, $C_1$–$C_8$alkyl, benzyl or a group of formula (IV);

q is 1 or 2 and, when q is 1, $R_{10}$ is $C_2$–$C_{10}$alkylene; and, when q is 2, $R_{10}$ is $C_2$–$C_4$alkanetriyl;

$R_{11}$ and $R_{12}$, which may be identical or different, are as defined above for $R_9$;

$R_{13}$ is $C_2$–$C_3$alkylene;

$R_{14}$ is as defined above for $R_9$;

$R_{15}$ is $C_2$–$C_3$alkylene;

$R_{20}$ and $R_{21}$, which may be identical or different, are one of the groups of formula (IIa)–(IIc) or a group

or $R_{27}O$— in which $R_{25}$, $R_{26}$ and $R_{27}$, which may be identical or different, are as defined above for $R_9$, or $R_{27}$ can also be phenyl or di-t-butylphenyl;

A' has one of the definitions of A;

$R_{22}$ is $C_2$–$C_3$alkylene;

$L_1$ has any one of the meanings given to $R_1$ or is a group $(R_{28})_3SiO$— where $R_{28}$ is methyl;

$L_2$ is hydrogen, methyl, ethyl, a group $(R_{28})_3Si$— with $R_{28}$ as defined above, or, when n is zero and $R_1$ and $L_1$ are methyl, $L_2$ is also a group of formula (V), and, when m+n is a number from 3 to 10, $L_1$ and $L_2$ together can also represent a direct linkage.

5. A compound of formula (I) according to claim 1, in which $R_5$ and $R_{23}$, which may be identical or different, are hydrogen, $C_1$–$C_4$alkyl, $C_1$–$C_{12}$alkoxy, $C_5$–$C_{12}$cycloalkoxy, benzyl either unsubstituted or substituted with 1, 2 or 3 $C_1$–$C_4$alkyls; or $C_1$–$C_4$acyl.

6. A compound of formula (I) according to claim 1, in which m+n is a number from 1 to 60 and n varies from zero to 90% of the sum m+n;

$R_1$ and $R_3$, which may be identical or different, are methyl, methoxy or OH;

$R_2$ is trimethylene;

G is one of the groups of formula (IIa), (IIc) or (IId);

$R_5$ is hydrogen or methyl;

E is —CO— and p is 1;

$R_6$ is hydrogen;

$R_4$ is hydrogen, $C_1$–$C_{18}$alkyl, one of the groups of formula (IIIa), (IIIb), (IIIc) or (IIIg);

$R_7$ is a group of formula (IV);

$R_8$ is trimethylene;

$R_9$ is a group of formula (IV);

$R_{23}$ is hydrogen or methyl;

A is —O— or —NR$_{24}$— where $R_{24}$ is hydrogen, $C_1$–$C_4$alkyl or a group of formula (IV);

q is 1 or 2 and, when q is 1, $R_{10}$ is $C_2$–$C_{10}$alkylene; and, when q is 2, $R_{10}$ is $C_2$–$C_{14}$alkanetriyl;

$R_{11}$ and $R_{12}$, which may be identical or different, are as defined above for $R_9$;

$R_{13}$ is trimethylene;

$R_{20}$ and $R_{21}$, which may be identical or different, are a group

in which $R_{25}$ and $R_{26}$, which may be identical or different, are $C_1$–$C_4$alkyl or a group of formula (IV);

A' has one of the definitions of A;

$R_{22}$ is trimethylene;

$L_1$ has any one of the meanings given to $R_1$ or is a group $(R_{28})_3SiO$— where $R_{28}$ is methyl;

$L_2$ is hydrogen, methyl, a group $(R_{28})_3Si$— with $R_{28}$ as defined above, or, when n is zero and $R_1$ and $L_1$ are methyl, $L_2$ is also a group of formula (V), and, when m+n is a number from 3 to 10, $L_1$ and $L_2$ together can also represent a direct linkage.

7. A composition comprising synthetic polymer susceptible to degradation induced by light, heat or oxidation and at least one compound of formula (I) according to claim 1.

8. A composition according to claim 7 comprising, in addition to the compound of formula (I), other conventional additives for synthetic polymers.

9. A composition according to claim 7 in which the synthetic polymer is a polyolefin.

10. A composition according to claim 7 in which the synthetic polymer is polyethylene or polypropylene.

11. A method for stabilizing a synthetic polymer against degradation induced by light, heat or oxidation, which comprises incorporating in said synthetic polymer at least one compound of formula (I) as defined in claim 1.

* * * * *